United States Patent [19]
Sinofsky et al.

[11] Patent Number: 6,004,261
[45] Date of Patent: Dec. 21, 1999

[54] FORMED-IN-PLACE ENDOVASCULAR STENT AND DELIVERY SYSTEM

[75] Inventors: Edward L. Sinofsky, Peabody, Mass.; Scott J. Solano, Lake Jackson, Tex.; James F. Crittenden, Hollis, N.H.

[73] Assignee: C. R. Bard, Inc., Murray Hill, N.J.

[21] Appl. No.: 08/799,991

[22] Filed: Feb. 13, 1997

Related U.S. Application Data

[63] Continuation of application No. 08/073,277, Jun. 4, 1993, abandoned.

[51] Int. Cl.$^6$ ................... A61F 1/00; A61F 2/15
[52] U.S. Cl. .................. 600/36; 623/1; 623/12; 604/96; 604/101; 128/395
[58] Field of Search ............. 623/1, 12; 600/36; 604/96, 101; 128/395, 398, 899, 397; 606/7, 8, 13–15, 192–195

[56] References Cited

U.S. PATENT DOCUMENTS

| | | |
|---|---|---|
| 3,173,418 | 3/1965 | Baran . |
| 3,563,925 | 2/1971 | Kliment et al. ............. 260/8 |
| 3,625,745 | 12/1971 | Wright ................. 117/93.31 |
| 3,808,113 | 4/1974 | Okamura et al. . |
| 3,949,073 | 4/1976 | Daniels et al. ............ 424/117 |
| 4,060,081 | 11/1977 | Yannas et al. ............ 128/156 |
| 4,319,363 | 3/1982 | Ketharanathan ............. 3/1.4 |
| 4,378,017 | 3/1983 | Kosugi et al. ............. 424/35 |
| 4,390,519 | 6/1983 | Sawyer .................. 424/28 |
| 4,403,612 | 9/1983 | Fogarty . |
| 4,417,576 | 11/1983 | Baran .................. 128/207.15 |
| 4,423,725 | 1/1984 | Baran et al. ............. 128/207.15 |
| 4,445,892 | 5/1984 | Hussein et al. ............ 604/101 |
| 4,485,096 | 11/1984 | Bell .................... 424/95 |
| 4,503,569 | 3/1985 | Dotter .................... 3/1.4 |
| 4,553,545 | 11/1985 | Maass et al. . |
| 4,553,974 | 11/1985 | Dewanjee ................ 8/94.11 |
| 4,577,631 | 3/1986 | Kreamer . |
| 4,578,067 | 3/1986 | Cran, Jr. ................ 604/380 |
| 4,589,882 | 5/1986 | Urry .................... 623/11 |
| 4,597,762 | 7/1986 | Walter et al. ............. 623/1 |
| 4,605,406 | 8/1986 | Cahalan et al. ............. 623/1 |
| 4,641,653 | 2/1987 | Rockey .................. 604/96 |
| 4,642,118 | 2/1987 | Kuroyanagi et al. .......... 623/15 |
| 4,695,281 | 9/1987 | Miyata et al. ............. 623/11 |
| 4,704,131 | 11/1987 | Noishiki et al. ............ 623/66 |
| 4,708,718 | 11/1987 | Daniels ............... 128/DIG. 8 |
| 4,732,152 | 3/1988 | Wallsten et al. . |
| 4,733,665 | 3/1988 | Palmaz . |
| 4,740,207 | 4/1988 | Kreamer .................. 623/1 |
| 4,763,653 | 8/1988 | Rockey .................. 606/194 |
| 4,773,899 | 9/1988 | Spears .................. 604/96 |
| 4,799,479 | 1/1989 | Spears ................... 606/7 |
| 4,842,575 | 6/1989 | Hoffman, Jr. et al. ....... 600/36 |
| 4,878,492 | 11/1989 | Sinofsky et al. .......... 128/395 |
| 4,969,912 | 11/1990 | Kelman et al. .......... 128/DIG. 8 |
| 4,994,033 | 2/1991 | Shockey et al. .......... 606/194 |
| 5,019,075 | 5/1991 | Spears et al. ............. 606/7 |
| 5,213,580 | 5/1993 | Slepian et al. . |
| 5,328,471 | 7/1994 | Slepian . |

FOREIGN PATENT DOCUMENTS 8912478  12/1989  WIPO .

OTHER PUBLICATIONS

*Science*, vo. 232, Jun. 13, 1986, pp. 1421–1422.

*Primary Examiner*—Gary Jackson
*Assistant Examiner*—Nancy Mulcare
*Attorney, Agent, or Firm*—Arthur Z. Bookstein

[57] ABSTRACT

An uncured or partially cured, collagen-based material is delivered to a selected site in a blood vessel and is crosslinked in the blood vessel by laser energy or other suitable energy to form an endovascular stent. The collagen-based material can be delivered to the blood vessel as a coating on an inflatable balloon mounted on the distal end of a catheter. The collagen-based material can also be delivered to the blood vessel in liquid form. The liquid collagen-based material is forced through a porous balloon to form either an imperforate tubular configuration or a tubular mesh configuration. The collagen-based material is preferably crosslinked by laser radiation carried through an optical fiber to a diffusing tip located within the balloon.

29 Claims, 3 Drawing Sheets

27
FORMED-IN-PLACE ENDOVASCULAR STENT AND DELIVERY SYSTEM

This application is a continuation, of application Ser. No. 08/073,3277, filed Jun. 4, 1993, now abandoned.

FIELD OF THE INVENTION

This invention relates to an endovascular stent for transluminal delivery to a blood vessel and, more particularly, to a collagen-based endovascular stent and to techniques for delivery of the stent. An uncured or partially cured, collagen-based material is delivered to a selected site in a blood vessel and is crosslinked in the blood vessel by laser energy to form an endovascular stent.

BACKGROUND OF THE INVENTION

Balloon angioplasty is utilized to treat coronary arteries narrowed by plaque deposits. A catheter having an inflatable balloon secured to its distal end is advanced through the artery to the narrowed region. The balloon is inflated, causing the narrowed, or stenosed, region of the artery to be expanded. The balloon is then deflated and withdrawn.

A serious problem associated with balloon angioplasty has been the occurrence in up to 30% of the cases of so-called restenosis, either immediately after the procedure or within about six months. Immediate restenosis, also known as abrupt reclosure, results from flaps or segments of plaque and plaque-ridden tissue which are formed during balloon angioplasty and which can block the artery. Such blockage of the artery requires emergency surgery and often results in death. Furthermore, a surgical team is required to stand by during the balloon angioplasty procedure. Restenosis at a later time results from causes that are not totally known. Thrombus formation is believed to play an important part. Often, repeat balloon angioplasty or surgery is required, and another episode of restenosis may occur.

One approach to dealing with the problem of restenosis is to maintain a passage through the artery with an endovascular stent. The stent is a generally tubular device which is placed inside the blood vessel after balloon angioplasty or some other type of angioplasty has been completed. The stent has sufficient strength and resiliency to resist restenosis and to maintain a passage through the vessel. A catheter is typically used to deliver the stent to the stenosed site. U.S. Pat. No. 4,733,665, issued Mar. 29, 1988 to Palmaz, discloses a vascular stent comprising an expandable wire mesh tube. The stent is positioned over an inflatable balloon secured to a catheter and is advanced to the stenosed region. The balloon is inflated, thereby expanding the stent into contact with the vessel wall. The elastic limit of the wire mesh is exceeded when the balloon is expanded, so that the stent retains its expanded configuration. U.S. Pat. No. 4,503, 569, issued Mar. 12, 1985 to Dotter, discloses a shape memory alloy stent that is advanced to a stenosed region on a catheter. The stent has the form of a coil spring. After positioning, the stent is heated with a hot fluid causing the shape memory alloy to expand into contact with the blood vessel. U.S. Pat. No. 4,740,207, issued Apr. 26, 1988 to Kreamer, discloses a plastic graft for repair of the vascular system. A catheter is suggested for placement of the graft in a coronary artery. Stents for placement in blood vessels are also disclosed in U.S. Pat. No. 4,553,545, issued Nov. 19, 1985 to Maass et al and U.S. Pat. No. 4,732,152, issued Mar. 22, 1988 to Wallsten et al. U.S. Pat. No. 4,577,631 issued Mar. 25, 1986 to Kreamer, discloses a Dacron blood vessel graft that is coated with an adhesive. The Kreamer patent states that the adhesive may be activated by ultraviolet or ultrasonic energy after placement in the aorta.

All known prior art vascular stents have been fabricated of metal or plastic and remain in the blood vessel indefinitely. The long term effects of such devices are not well known. Furthermore, such devices have a fixed range of expansion within the blood vessel. In some cases, the stent may be too small in diameter, even after expansion, to be affixed to the vessel wall, and in other cases the stent may expand to such a diameter that the vessel is damaged or ruptured. In either case, improperly sized or positioned prior art stents require surgery for removal.

It has been proposed in the prior art to use collagens and collagen-based compositions in skin grafts, bandages and vascular prostheses. An advantage of using collagen in such devices is that collagen occurs naturally in the human body, and the graft or prosthesis is eventually absorbed into the tissue to which it is attached. U.S. Pat. No. 4,319,363, issued Mar. 16, 1982 to Ketharanathan, discloses a vascular prosthesis for use as a surgical graft. The prosthesis comprises a tubular wall of Type I collagenous tissue. U.S. Pat. No. 4,390,519, issued Jun. 28, 1983 to Sawyer, discloses a bandage wherein a collagen or collagen-like substance is incorporated into the pad or sponge of the bandage. U.S. Pat. No. 4,642,118, issued Feb. 10, 1987 to Kuroyanagi et al, discloses a man-made skin including a collagen sponge layer and a poly-alpha-amino acid membrane. U.S. Pat. No. 3,808,113, issued Apr. 30, 1974 to Okamura et al discloses a method for manufacturing medical articles comprising a polymer coated with collagen. In one step of the process, the collagen is irradiated with radioactive rays, an electron beam or ultraviolet radiation to fix the collagen layer.

U.S. Pat. No. 4,417,576, issued Nov. 29, 1983 to Baran, discloses a double wall surgical cuff for introduction into a body passage. The outer cuff is porous, and a sponge material is positioned between the inner and outer cuffs. A surgical fluid such as an anesthetic is absorbed by the sponge material. When the inner cuff is inflated, the fluid is driven through the porous outer cuff to the walls of the body passage.

It is a general object of the present invention to provide improved endovascular stents.

It is another object of the present invention to provide a collagen-based endovascular stent or to use collagen as a temporary adhesive until the body incorporates it.

It is another object of the present invention to provide an endovascular stent that is formed into its final configuration at a site in a blood vessel where it is to be placed.

It is a further object of the present invention to provide methods and apparatus for delivery and placement of a collagen-based endovascular stent.

It is yet another object of the present invention to provide an endovascular stent which is crosslinked into its final configuration in a blood vessel by application of energy.

It is still another object of the present invention to provide an endovascular stent that is formed in place by the application of laser energy to a collagen-based material.

SUMMARY OF THE INVENTION

According to the present invention, these and other objects and advantages are achieved in a method for treating a selected region of a blood vessel. The method comprises the steps of positioning a collagen-based material in the blood vessel. The collagen-based material is in a state that is less than fully crosslinked. Energy is applied to the collagen-based material to cause crosslinking thereof and formation of a stent in the blood vessel. The collagen-based material is formed into a shape having a lumen therethrough. Preferably, the collagen-based material is positioned in the blood vessel by advancing a catheter carrying the collagen-based material through the blood vessel to the selected region.

In one embodiment of the invention, a catheter having an inflatable balloon is used for delivery of the collagen-based material. A layer of collagen-based material is deposited on the outer surface of the balloon. The balloon is inflated prior to the step of applying energy, causing the layer of collagen-based material to be brought into contact with an inside surface of the blood vessel. Energy is applied through the balloon, causing the layer of collagen-based material to be completely crosslinked. As a result, the layer of collagen-based material becomes more rigid and forms a stent in the blood vessel.

In another embodiment of the invention, a catheter having an outer balloon with openings and an inflatable inner balloon is used for delivery of the collagen-based material. The balloons are advanced to the selected region of the blood vessel. A collagen-based material in liquid form is injected into a space between the inner and outer balloons, either before or after the balloons are positioned in the selected region of the blood vessel. The liquid collagen-based material can be injected through a lumen in the catheter to the space between the balloons. The collagen-based material is forced through the openings in the outer balloon by inflating the inner balloon. In a preferred embodiment, the openings in the outer balloon are arranged in a grid or mesh pattern. After the collagen-based material has been forced through the openings in the outer balloon, energy is applied to the collagen-based material, causing it to be crosslinked. The crosslinked collagen-based material is sufficiently rigid to form a stent in the blood vessel.

Preferably, laser energy is carried through an optical fiber terminated in a diffusing tip located within the balloon. The laser energy is directed outwardly through the balloon wall by the diffusing tip, causing crosslinking of the collagen-based material. In other embodiments, the collagen-based material is crosslinked by thermal energy, which can be generated by a resistive heating element located within the balloon, by radio frequency energy from outside the body or by beta rays.

According to another aspect of the invention, there is provided an endovascular stent for positioning in a selected region of the blood vessel. The stent comprises a collagen-based body that is crosslinked in the selected region by the application of energy. The collagen-based body has a lumen therethrough and is preferably crosslinked when irradiated by laser energy.

According to still another aspect of the invention, there is provided a method for treating a wound comprising the steps of positioning on the wound a collagen-based material that can be crosslinked by the application of laser energy, and applying laser energy to the collagen-based material to cause crosslinking thereof and formation of a protective covering on the wound.

The present invention provides a collagen-based stent that is formed in place in the blood vessel, thus insuring that the stent is properly sized and shaped. The collagen-based stent is gradually absorbed into and becomes a part of the blood vessel, thus avoiding problems of biological compatibility.

BRIEF DESCRIPTION OF THE DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figure 1A:
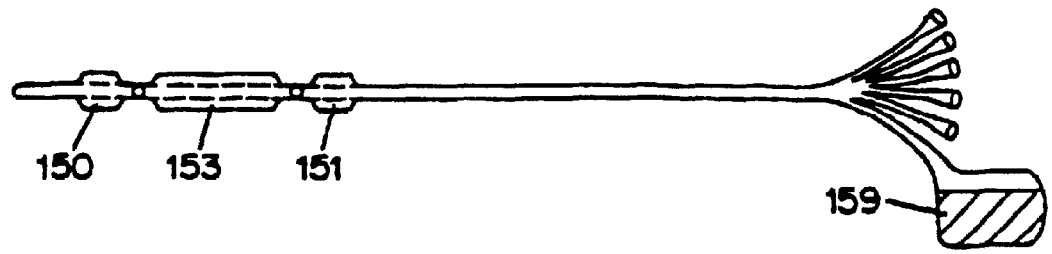
FIG. 1 is an enlarged, cross-sectional view of an artery having a collagen-based stent positioned therein.
Figure 1B:
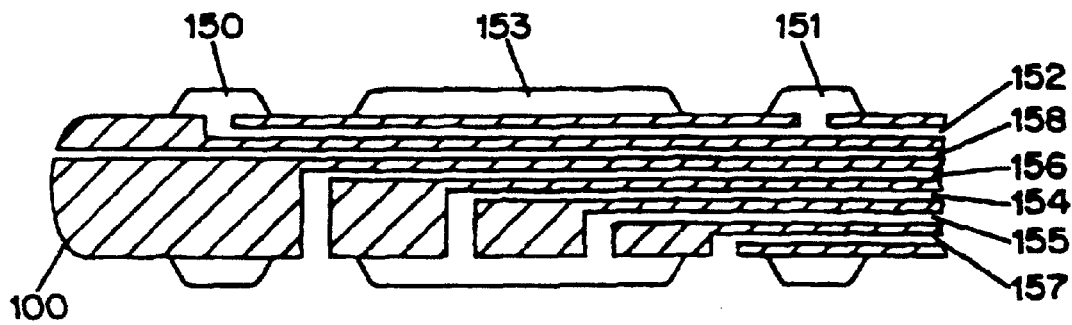

In accordance with the present invention, there is provided a formed-in-place endovascular stent for use in a blood vessel, typically an artery. The stent is composed at least in part of collagen to ensure compatibility with the blood vessel. As shown in FIG. 1, an endovascular stent 10 is positioned in an artery 12 at a selected location that may have plaque deposits 14. Typically, balloon angioplasty has been utilized to provide a widened passage through plaque deposits 14.

In an important feature of the invention, a collagen-based material for stent 10 is delivered to the selected location in artery 12 in the form of a liquid or a pliable solid. The liquid or pliable solid collagen-based material is uncured or partially cured until it is positioned at the selected location. The collagen-based material is formed at the selected location into the desired stent configuration. Typically, the stent 10 has a generally tubular configuration including a wall 16 which defines a lumen 18. The stent 10 may have an irregular shape to conform to the interior of artery 12. After the collagen-based material has been formed into the desired configuration in artery 12, energy, typically laser energy or thermal energy, is applied thereto, causing the collagen-based material to be crosslinked. Crosslinking of the collagen-based material causes it to become more rigid and to retain its shape, and to adhere to the wall of the artery. Techniques for delivery, formation and curing of stent 10 are described in detail hereinafter.

Figure 2:
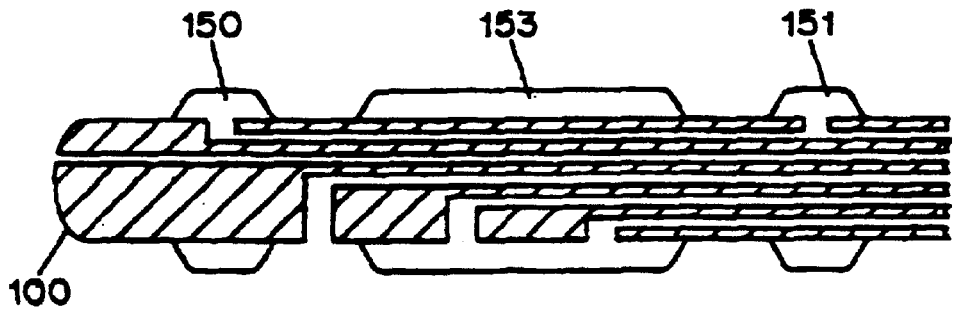
FIG. 2 is a an illustration of a laser balloon catheter suitable for delivery of a collagen-based stent.

The collagen-based material is advantageously delivered to the selected region of the artery with a laser balloon catheter as shown in FIG. 2. An elongated, flexible tube 20 has a laser balloon assembly 22 at its distal end and connectors 24, 26, 28 and 30 at its proximal end. The laser balloon assembly 22 includes an optical fiber tip assembly 34 (FIG. 3), for emitting laser radiation, a distal extension 36 of tube 20 for a guidewire (not shown) and for carrying a fluid to the treatment region, and a balloon 40 which is inflated and deflated from the proximal end of the flexible tube 20. An optical fiber extends from connector 30 through a lumen in the flexible tube 20 and terminates in optical fiber tip assembly 34.

The optical fiber tip assembly 34 is a diffusing tip which directs laser energy outwardly through balloon 40 in a generally uniform cylindrical radiation pattern. The balloon 40 is preferably fabricated of polyethylene terephthalate (PET). In one embodiment, the optical fiber tip assembly 34 includes a tapered optical fiber that has a spiral shape around distal extension 36 to prevent shadowing. Further details regarding the construction of the laser balloon catheter are provided in pending application Ser. No. 106,609, filed Oct. 8, 1987, which is hereby incorporated by reference.

A collagen-based material 46 is adhered to the outer surface of balloon 40. The collagen-based material 46 is pliable and resilient so that the balloon 40 can be deflated for delivery to the selected region of the artery. When the balloon 40 is deflated, the collagen-based material 46 remains adhered to the balloon surface and collapses with the balloon. When the balloon 40 is inflated, the collagen-based material 46 is sufficiently resilient and pliable to unfold with the balloon. Preferably, the collagen-based material 46 is formed as a coating on balloon 40.

In use, the laser balloon catheter shown in FIGS. 2 and 3 is advanced through an artery to a stenosed region that has previously been treated by balloon angioplasty. The balloon 40 carrying collagen-based material 46 is positioned in the stenosed region. The balloon 40 is inflated so that the collagen-based material 46 is brought into contact with the inner surface of artery 12. After balloon 40 is inflated, laser energy from an external source is supplied through connector 30 and the optical fiber in tube 20 to tip assembly 34. The laser energy is diffused outwardly in a generally uniform cylindrical pattern causing collagen-based material 46 to be crosslinked. When the collagen-based material is crosslinked, it becomes more rigid and forms a stent in the artery, as shown in FIG. 1. The laser energy is then turned off, and the stent is allowed to cool. After cooling, the balloon 40 is deflated. Since the stent 10 is now more rigid, it peels off the balloon and remains in place on the wall of artery 12 rather than collapsing with balloon 40. The laser balloon catheter is then withdrawn leaving stent 10 to maintain a passage and prevent flaps of plaque 14 from blocking the artery 12. Eventually, the stent 10 is absorbed into the tissue of the artery 12 so that a widened passage is maintained without the requirement for a metallic stent.

Figure 4:
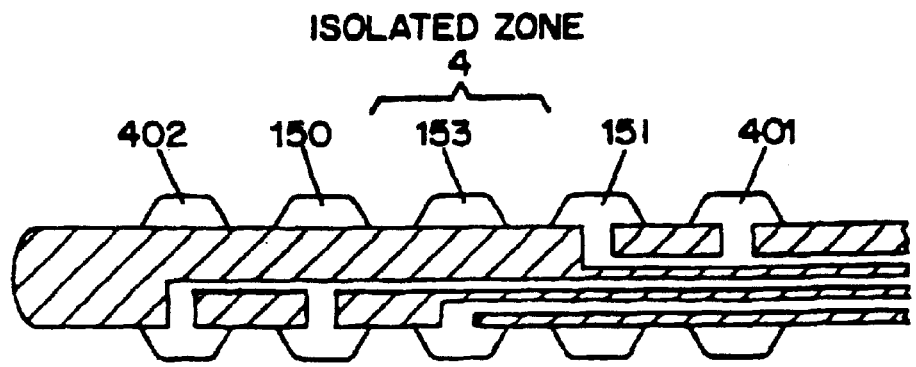
FIG. 4 is an enlarged, cross-sectional view of the distal end of the laser balloon catheter in accordance with another technique for delivery of a collagen-based stent.
Figure 3A:
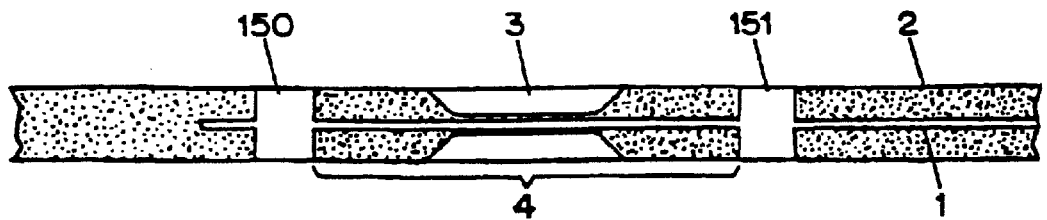
FIG. 3 is an enlarged, cross-sectional view of the distal end of the laser balloon catheter taken along the lines 3—3 of FIG. 2 and illustrating a technique for delivery of a collagen-based stent.
Figure 3B:
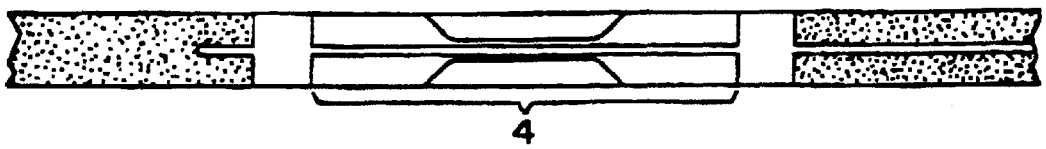
Figure 3C:
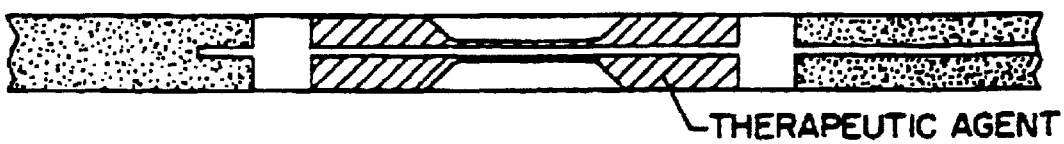
Figure 3D:
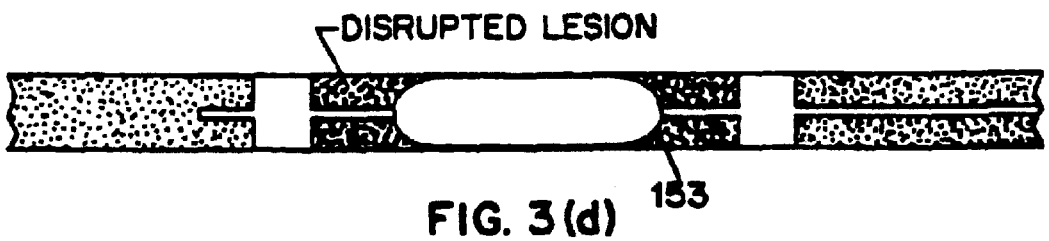
Figure 3E:
Figure 3F:
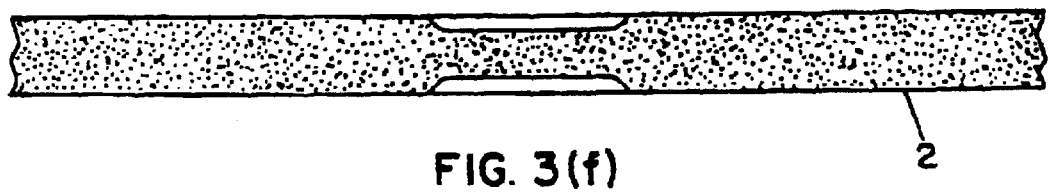
Figure 5:
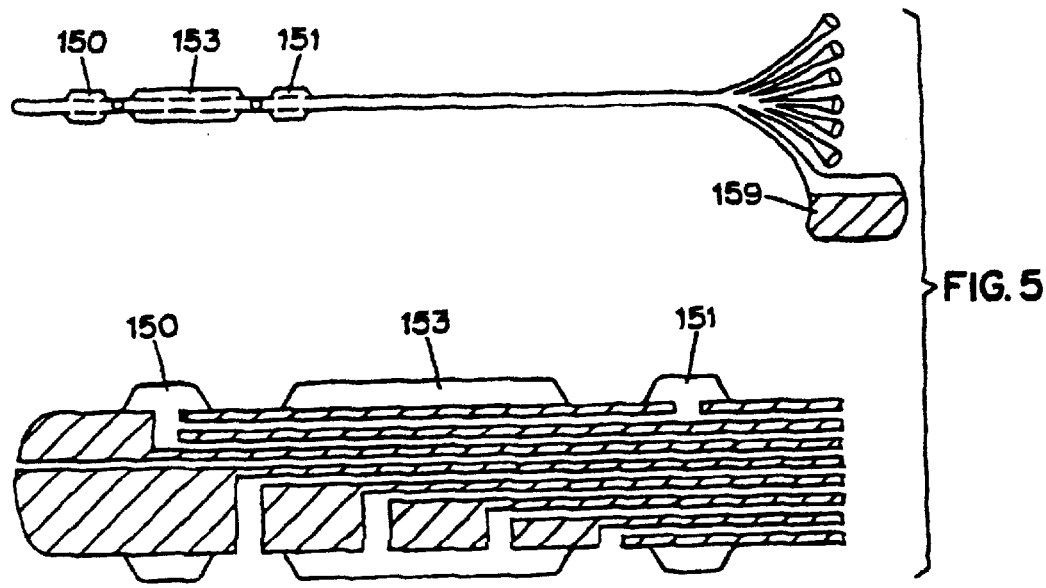
FIGS. 5–7 are fragmentary views of the outer balloon of FIG. 4 illustrating a pattern of openings in the balloon.

An alternative laser balloon catheter for delivery of a formed-in-place endovascular stent is shown in FIGS. 4 and 5. The device is a laser balloon catheter having a laser balloon assembly 50 as shown in FIG. 4. The laser balloon assembly 50 includes optical fiber tip assembly 34 and central shaft 36 at the distal end of flexible tube 20. An inner balloon 52 is sealed at one end to tube 20 and at the other end to central shaft 36. Balloon 52 can be inflated and deflated from the proximal end of tube 20. An outer balloon 54 surrounds inner balloon 52 and is sealed to flexible tube 20 and to central shaft 36 in a manner similar to inner balloon 52. A port 55 interconnects a lumen (not shown) in flexible tube 20 and a space 56 between balloons 52 and 54. Outer balloon 54 includes a multiplicity of pores or openings 60 (FIG. 5). Preferably, the openings 60 have a diameter of about 0.005-inch or less, depending on the viscosity of the collagen-based material.

The space 56 between inner balloon 52 and outer balloon 54 is filled with a liquid collagen-based material. The collagen-based material has sufficient viscosity to remain in the space 56 when inner balloon 52 is deflated. When inner balloon 52 is inflated, the collagen-based material is forced through the openings 60 in outer balloon 54 to form a layer of collagen-based material surrounding outer balloon 54. Since inner balloon 52 is inflated, the layer of collagen-based material is pushed outwardly into contact with the inside surface of the artery. Laser energy is then supplied through the optical fiber in flexible tube 20 to tip assembly 34. The laser energy is directed outwardly by tip assembly 34 through balloons 52 and 54, causing the layer of collagen-based material to be crosslinked. When the collagen-based material is crosslinked, it becomes more rigid and forms a stent in the selected region of the artery. The balloons 52 and 54 are then deflated, and the laser balloon catheter is withdrawn from the artery.

In one embodiment, the liquid collagen-based material is injected through port 55 into the space 56 between balloons 52 and 54 before the laser balloon assembly 50 is advanced to the stenosed region of the artery. In a second embodiment, the liquid collagen-based material is injected through port 55 into the space 56 through one of the lumens in flexible tube 20 after the laser balloon assembly 50 has been positioned in the stenosed region of the artery.

The openings 60 in outer balloon 54 can be uniformly distributed over its surface with a spacing that is sufficiently close to permit the liquid collagen-based material to flow together after it passes through the openings. In this case, the collagen-based material forms a continuous layer on the wall of the artery. For an imperforate tubular stent, the openings 60 should have a uniform spacing of 5 to 10 times the diameter of openings 60. In another embodiment illustrated in FIG. 5, openings 60 in outer balloon 54 are patterned to form a mesh, grid or other desired pattern. When the liquid collagen-based material flows through openings 60, it forms a pattern that is determined by the pattern of openings 60. After crosslinking by laser radiation, the stent retains the pattern defined by openings 60. Thus, the stent may have a mesh or grid configuration which allows unobstructed blood flow to side branch arteries that are located at the site of the stent. For a mesh or grid configuration, the openings 60 should have a spacing of about 5 times the diameter of openings 60 along the lines of mesh and a spacing between lines of about 20 times the diameter of openings 60.

Types I–V collagens can be utilized for the formed-in-place endovascular stent described herein, since these collagens can be crosslinked. Type III collagens derived from the human cardiovascular system are preferred. Also, a number of Type I collagens can be utilized. A collagen derived from chicken ligaments and rat tail (99% pure) has been used in vitro. An example of preparation of a collagen stent is described below.

1. Type I bovine corium collagen available from Collagen Corporation, Palo Alto, Calif., is slowly dissovled in a 1% solution of glutaraldehyde (Grade 1-Sigma Corporation, St. Louis, Mo.), causing some crosslinking to occur in the collagen.
2. The solution is gently heated for 10–20 hours to remove non-biocompatible materials.
3. The solution is centrifuged for about 2 minutes at 7500 rpm to concentrate the collagen.
4. After the supernatant has been discarded, the sediment is introduced into the vascular system by a porous laser balloon catheter as shown in FIGS. 4 and 5 and described hereinabove. When the selected region of the artery is reached, laser energy at a wavelength of 350 nanometers or infrared radiation at 0.8 to 2.5 micrometers is applied through the balloon wall to complete the crosslinking process.
5. The stent thus formed remains in place from 20–90 days and is gradually absorbed by the body.

The collagen can be dissolved in any aldehyde containing solution since crosslinking occurs between amino groups. The amount of crosslinking can be controlled by varying the concentration of the aldehyde, the duration of exposure of the collagen to the aldehyde, or adjusting the number of available amino groups. Crosslinking is caused by the formation of covalent bonds and may be either intramolecular or intermolecular, depending on the type of collagen. Crosslinking increases the rigidity and the mechanical strength of the collagen, as described in *Science,* Vol. 232, Jun. 13, 1986, pp. 1421–1422.

Light energy at various wavelengths can be utilized to effect crosslinking at the selected region of the artery. While ultraviolet radiation is preferable, visible and infrared radiation can also be utilized, depending on the collagen selected. In addition, thermal energy from any suitable source, such as a resistive heating element located within the inflatable balloon, can be utilized to effect crosslinking. External radio frequency energy or beta rays can also be used to effect crosslinking.

The invention has been described thus far in connection with formation of an endovascular stent utilized in blood vessels. The techniques described herein can also be utilized for treatment of wounds on the skin. A layer of collagen-based material with or without a support layer, such as PET, is positioned over the wound. The collagen-based material is in an uncured or partially cured state. Laser radiation is then applied to the collagen-based material causing crosslinking thereof and formation of a semi-rigid protective layer.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for treating a selected region of a blood vessel, comprising the steps of:
   positioning a material in the blood vessel, said material being in a state that is less than fully crosslinked, the step of positioning a material including the step of forming the material into a desired shape having a lumen therethrough; and
   applying energy to the material to cause crosslinking thereof and formation of a stent in the blood vessel.

2. A method as defined in claim 1 wherein the material in the positioning and forming steps is a collagen-based material.

3. A method as defined in any one of claims 1 or 2 wherein the step of applying energy includes the step of applying light energy.

4. A method as defined in any one of claims 1 or 2 wherein the step of applying energy includes the step of applying laser energy.

5. A method as defined in any one of claims 1 or 2 wherein the step of applying energy includes the step of applying thermal energy.

6. Apparatus for treating a selected region of a blood vessel, comprising:
   a material that can be crosslinked by the application of radiation;
   means for positioning the material on a wall of a blood vessel in an uncured or partially cured state; and
   means for applying radiation to cause said material to become more rigid and thereby form in the blood vessel a stent having a structure and sufficient rigidity to support the blood vessel from within.

7. An apparatus as defined in claim 6 wherein the material that can be crosslinked by the application of radiation is a collagen-based material.

8. A combination of a stent and an apparatus for placing a stent in a selected region of a blood vessel, comprising;
   a flexible, elongated tube having an inflatable balloon at or near its distal end;
   a material that can be crosslinked by the application of radiation, said material being releaseably adhered to the outer surface of said balloon;
   means for inflating said balloon to thereby urge said material to contact with an inside surface of said blood vessel; and
   means for applying radiation through said balloon to said material with said balloon inflated to cause said material to become more rigid and thereby form a stent in the blood vessel.

9. Apparatus as defined in claim 8 wherein said means for applying radiation includes an optical diffusing tip in said balloon and an optical fiber for carrying laser energy from an external laser source to said diffusing tip, whereby laser energy is applied to said material through said balloon.

10. An apparatus as defined in claim 8 wherein the material than can be crosslinked by the application of radiation is a collagen-based material.

11. Apparatus for placing a material in a selected region of a blood vessel, comprising:
    a flexible, elongated tube having a distal end and a proximal end;
    an outer balloon having a plurality of openings affixed to said tube at or near the distal end thereof;
    an inflatable inner balloon located within said outer balloon;
    means for inflating said inner balloon to thereby force a material located between said inner and outer balloon through said openings; and
    means for applying radiation through said inner balloon and said outer balloon to said material after delivery through said openings, said radiation being selected to cure said material and form a stent having a structure and sufficient rigidity to support said blood vessel from within.

12. Apparatus as defined in claim 11 wherein said means for applying radiation includes an optical diffusing tip in said inner balloon and an optical fiber for carrying laser energy from an external laser source to said diffusing tip, whereby laser energy is applied to said material through said inner and outer balloons.

13. A method for placing a stent in a selected region of a blood vessel, comprising the steps of:
    advancing a collagen-based material through the blood vessel to the selected region in an uncured or partially uncured state;
    applying the collagen-based material to the wall of the blood vessel in the selected region; and
    applying energy to the collagen-based material to cause curing thereof and formation of a stent in the selected region.

14. A method as defined in claim 13 wherein the step of applying energy includes the step of applying laser energy.

15. A method for treating a selected region of a blood vessel, comprising the steps of:
    positioning a material in the blood vessel, said material being in a state that is less than fully crosslinked;
    forming the material into a desired shape for support of the blood vessel from within; and
    applying energy to the material in the desired shape to cause the material to have sufficient rigidity to support the blood vessel from within.

16. A method as defined in claim 15 wherein the material in the positioning, forming, and applying energy steps is a collagen-based material.

17. Apparatus for treating a selected region of a blood vessel comprising:
 a material being in a state that is less than fully crosslinked;
 means for positioning the material in the blood vessel;
 means for forming the material into a desired shape for support of the blood vessel from within; and
 means for applying energy to the material in the desired shape to cause the material to have sufficient rigidity to support the blood vessel from within.

18. An apparatus as defined in claim 17 wherein the material is a collagen-based material.

19. A method for treating a selected region of a blood vessel, comprising the steps of:
 positioning a material in the blood vessel, said material being in a state that is less than fully crosslinked, the step of positioning the material including the step of advancing a catheter having an inflatable balloon at or near its distal end through the blood vessel to the selected region, said catheter carrying the material in a state that is less than fully crosslinked to the selected region; and
 applying energy to the material to cause crosslinking thereof and formation of a stent in the blood vessel.

20. A method as defined in claim 19 wherein in the steps of positioning a material and applying energy to the material, the material is a collagen-based material.

21. A method as defined in any one of claims 11 or 12 wherein the step of advancing a catheter includes the step of depositing a layer of said material to an outer surface of said balloon.

22. A method as defined in claim 21 wherein the step of positioning a material further includes the step of inflating said balloon prior to the step of applying energy.

23. A method as defined in any one of claims 11 or 12 wherein the step of advancing a catheter includes the step of advancing a catheter having an outer balloon surrounding said inflatable balloon, said outer balloon having a plurality of openings.

24. A method as defined in claim 23 wherein the step of positioning a material further includes the steps of delivering said material to a space between said inflatable balloon and said outer balloon, and forcing said material through said openings in said balloon.

25. A method as defined in claim 24 wherein the step of forcing said material through said openings includes the step of inflating an inner balloon.

26. A method as defined in any one of claims 19 or 20 wherein the step of applying energy includes the step of directing laser energy through an optical fiber terminated in a diffusing tip that is positioned in said inflatable balloon.

27. A crosslinked endovascular stent placed in a selected region of a blood vessel comprising a pliable body having a lumen therethrough, said pliable body having a sufficient rigidity to support the blood vessel from within after being crosslinked at the selected region by the application of energy.

28. An endovascular stent as defined in claim 27 wherein the pliable body is made of a collagen-based material.

29. An endovascular stent as defined in any one of claims 27 or 28 wherein said body is fabricated of a collagen that is crosslinked when irradiated by laser energy.

* * * * *

UNITED STATES PATENT AND TRADEMARK OFFICE
CERTIFICATE OF CORRECTION

PATENT NO. : 6,004,261
DATED : December 21, 1999
INVENTOR(S) : Sinofsky *et al.*

It is certified that error appears in the above-identified patent and that said Letters Patent is hereby corrected as shown below:

On the title page, item [73],
In the Assignee

Please delete "C.R. Bard, Inc." and insert --Medtronic AVE, Inc.-- therefor.

Signed and Sealed this

Fifteenth Day of August, 2000

Attest:

Q. TODD DICKINSON

*Attesting Officer*   *Director of Patents and Trademarks*

UNITED STATES PATENT AND TRADEMARK OFFICE
CERTIFICATE OF CORRECTION

PATENT NO.   : 6,004,261
DATED        : December 21, 1999
INVENTOR(S)  : Sinofsky et al.

It is certified that error appears in the above-identified patent and that said Letters Patent is hereby corrected as shown below:

Title page,
Item [63], "Related U.S. Application Data" after "abandoned", please insert
-- , which is a continuation of Application No. 07/666,424, March 8, 1991, abandoned, which is a continuation of Application No. 07/345,110, April 28, 1989, abandoned --.

Column 1,
Line 5, after "abandoned", please insert -- , which is a continuation of Application No. 07/666,424, March 8, 1991, abandoned, which is a continuation of Application No. 07/345,110, April 28, 1989, abandoned --.

Figure 6:
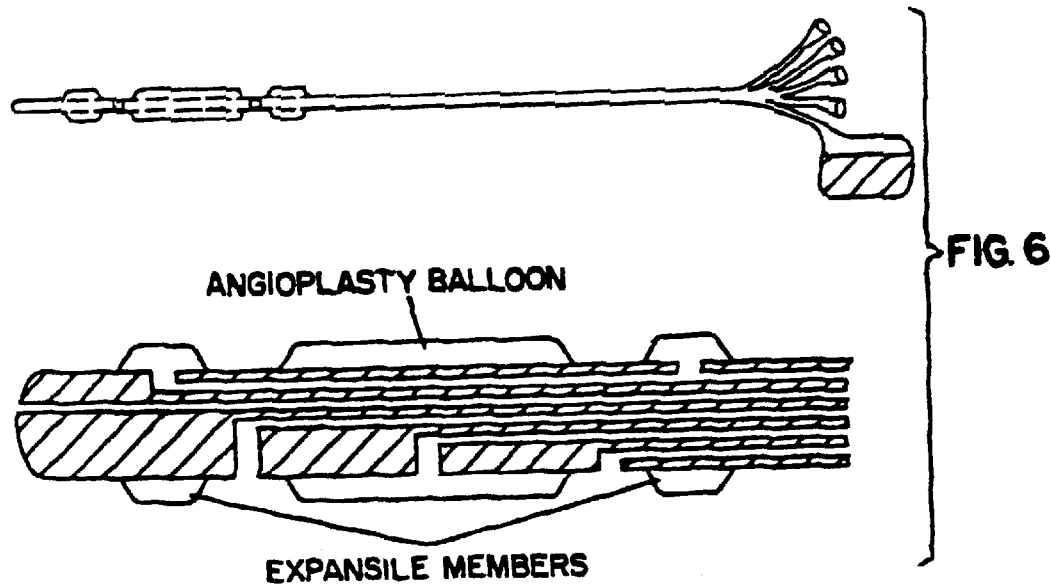
Figure 7:
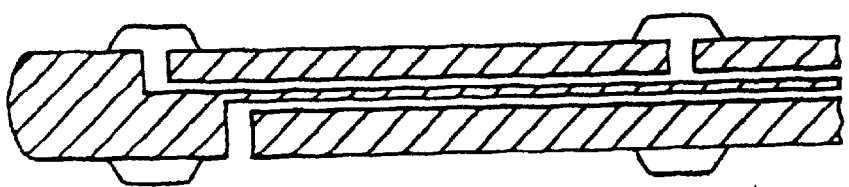

Column 4,
Line 16, please delete "FIGS. 5-7 are fragmentary views" and insert -- FIG. 5 is a fragmentary view --, therefor.

Column 8,
Line 4, please delete "releaseably" and insert -- releasably -- therefor.
Line 18, please delete "than" and insert -- that -- therefor.

Column 9,
Line 29, please delete "11 or 12" and insert -- 19 or 20 -- therefor.

Column 10,
Line 4, please delete "11 or 12" and insert -- 19 or 20 -- therefor.
Beginning at line 25, please delete claim 27, and insert:

-- 27. A crosslinkeable endovascular stent and endovascular delivery device for placement of the stent, in crosslinked form, in a blood vessel comprising, in combination:
a pliable body having a lumen therethrough, the body being formed from a material crosslinkable in response to application of energy, to a state having sufficient rigidity to support the blood vessel from within;
a delivery catheter having an expandable member thereon, the expandable member being disposed within the lumen of the crosslinkable stent;
the crosslinkable stent being radially expandable within the blood vessel by the expandable member on the catheter. --.

UNITED STATES PATENT AND TRADEMARK OFFICE
CERTIFICATE OF CORRECTION

PATENT NO. : 6,004,261
DATED : December 21, 1999
INVENTOR(S) : Sinofsky et al.

It is certified that error appears in the above-identified patent and that said Letters Patent is hereby corrected as shown below:

Column 10 cont'd.
Line 26, please delete "An endovascular stent" and insert -- A device -- therefor.
Line 29, please delete "An endovascular stent" and insert -- A device -- therefor.

Drawings,
Please delete FIGS. 1-7 and insert the following FIGS. 1-5, therefor.

Fig 1:

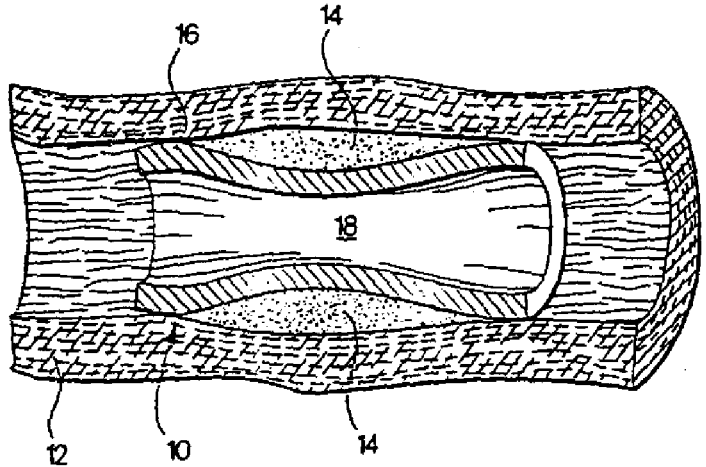

Fig. 1

UNITED STATES PATENT AND TRADEMARK OFFICE
CERTIFICATE OF CORRECTION

PATENT NO.    : 6,004,261
DATED         : December 21, 1999
INVENTOR(S)   : Sinofsky et al.

It is certified that error appears in the above-identified patent and that said Letters Patent is hereby corrected as shown below:

Figs. 2 and 3:

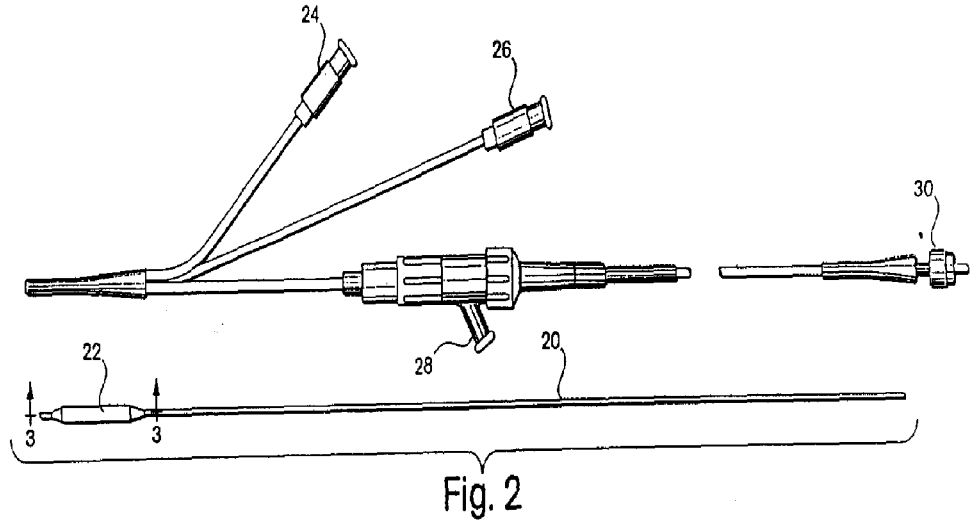

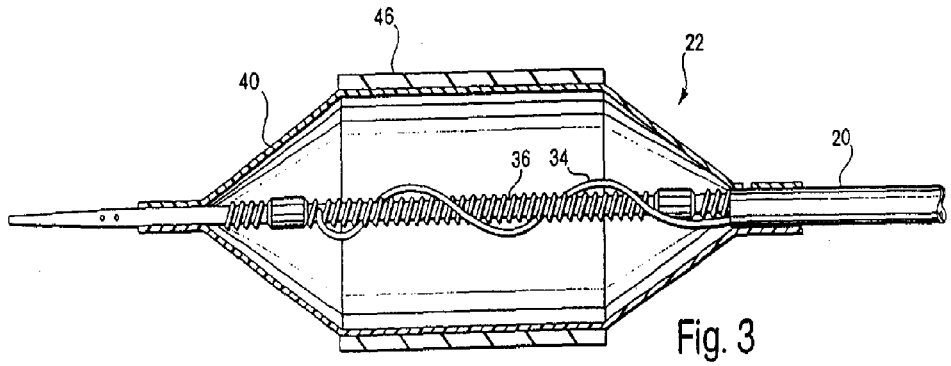

UNITED STATES PATENT AND TRADEMARK OFFICE
CERTIFICATE OF CORRECTION

PATENT NO.     : 6,004,261                                             Page 4 of 5
DATED          : December 21, 1999
INVENTOR(S)    : Sinofsky et al.

It is certified that error appears in the above-identified patent and that said Letters Patent is hereby corrected as shown below:

Figs. 4 and 5:

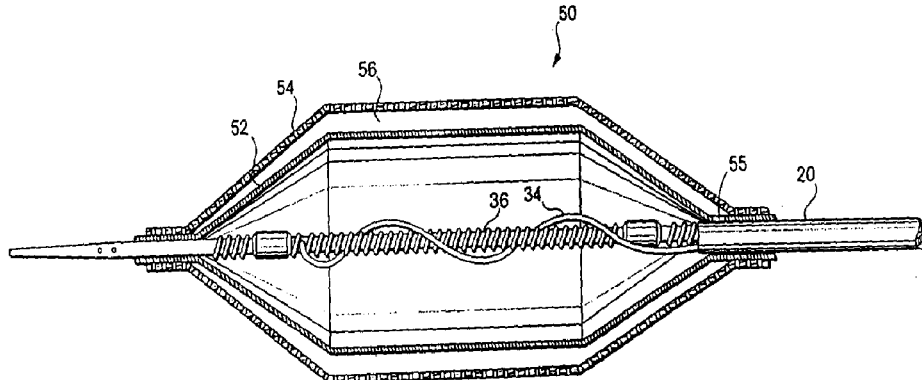

Fig. 4

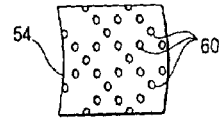

Fig. 5

Signed and Sealed this

Thirtieth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.     : 6,004,261
DATED          : December 21, 1999
INVENTOR(S)    : Sinofsky et al.

It is certified that error appears in the above-identified patent and that said Letters Patent is hereby corrected as shown below:

Title page,
Delete title page and insert the title page attached.
Item [63], "Related U.S. Application Data" after "abandoned", please insert -- , which is a continuation of Application No. 07/666,424, March 8, 1991, abandoned, which is a continuation of Application No. 07/345,110, April 28, 1989, abandoned --.

Column 1,
Line 5, after "abandoned", please insert -- , which is a continuation of Application No. 07/666,424, March 8, 1991, abandoned, which is a continuation of Application No. 07/345,110, April 28, 1989, abandoned --.

Column 4,
Line 16, please delete "FIGS. 5-7 are fragmentary views" and insert -- FIG. 5 is a fragmentary view --, therefor.

Column 8,
Line 4, please delete "releaseably" and insert -- releasably -- therefor.
Line 18, please delete "than" and insert -- that -- therefor.

Column 9,
Line 29, please delete "11 or 12" and insert -- 19 or 20 -- therefor.

Column 10,
Line 4, please delete "11 or 12" and insert -- 19 or 20 -- therefor.
Beginning at line 25, please delete claim 27, and insert:

-- 27. A crosslinkeable endovascular stent and endovascular delivery device for placement of the stent, in crosslinked form, in a blood vessel comprising, in combination:
a pliable body having a lumen therethrough, the body being formed from a material crosslinkable in response to application of energy, to a state having sufficient rigidity to support the blood vessel from within;
a delivery catheter having an expandable member thereon, the expandable member being disposed within the lumen of the crosslinkable stent;
the crosslinkable stent being radially expandable within the blood vessel by the expandable member on the catheter. --.

United States Patent [19]

Sinofsky et al.

[11] Patent Number: 6,004,261
[45] Date of Patent: Dec. 21, 1999

[54] FORMED-IN-PLACE ENDOVASCULAR STENT AND DELIVERY SYSTEM

[75] Inventors: Edward L. Sinofsky, Peabody, Mass.; Scott J. Solano, Lake Jackson, Tex.; James F. Crittenden, Hollis, N.H.

[73] Assignee: C. R. Bard, Inc., Murray Hill, N.J.

[21] Appl. No.: 08/799,991

[22] Filed: Feb. 13, 1997

Related U.S. Application Data

[63] Continuation of application No. 08/073,277, Jun. 4, 1993, abandoned.

[51] Int. Cl.[6] .............................. A61F 1/00; A61F 2/15
[52] U.S. Cl. ........................... 600/36; 623/1; 623/12; 604/96; 604/101; 128/395
[58] Field of Search .................... 623/1, 12; 600/36; 604/96, 101; 128/395, 398, 899, 397; 606/7, 8, 13–15, 192–195

[56] References Cited

U.S. PATENT DOCUMENTS

| Number | Date | Name | Class |
|---|---|---|---|
| 3,173,418 | 3/1965 | Baran . | |
| 3,563,925 | 2/1971 | Kliment et al. | 260/8 |
| 3,625,745 | 12/1971 | Wright | 117/93.31 |
| 3,808,113 | 4/1974 | Okamura et al. . | |
| 3,949,073 | 4/1976 | Daniels et al. | 424/117 |
| 4,060,081 | 11/1977 | Yannas et al. | 128/156 |
| 4,319,363 | 3/1982 | Ketharanathan | 3/1.4 |
| 4,378,017 | 3/1983 | Kosugi et al. | 424/35 |
| 4,390,519 | 6/1983 | Sawyer | 424/28 |
| 4,403,612 | 9/1983 | Fogarty . | |
| 4,417,576 | 11/1983 | Baran | 128/207.15 |
| 4,423,725 | 1/1984 | Baran et al. | 128/207.15 |
| 4,445,892 | 5/1984 | Hussein et al. | 604/101 |
| 4,485,096 | 11/1984 | Bell | 424/95 |
| 4,503,569 | 3/1985 | Dotter | 3/1.4 |
| 4,553,545 | 11/1985 | Maass et al. . | |
| 4,553,974 | 11/1985 | Dewanjee | 8/94.11 |
| 4,577,631 | 3/1986 | Kreamer . | |
| 4,578,067 | 3/1986 | Cran, Jr. | 604/380 |
| 4,589,882 | 5/1986 | Urry | 623/11 |
| 4,597,762 | 7/1986 | Walter et al. | 623/1 |
| 4,605,406 | 8/1986 | Cahalan et al. | 623/1 |
| 4,641,653 | 2/1987 | Rockey | 604/96 |
| 4,642,118 | 2/1987 | Kuroyanagi et al. | 623/15 |
| 4,695,281 | 9/1987 | Miyata et al. | 623/11 |
| 4,704,131 | 11/1987 | Noishiki et al. | 623/66 |
| 4,708,718 | 11/1987 | Daniels | 128/DIG. 8 |
| 4,732,152 | 3/1988 | Wallsten et al. . | |
| 4,733,665 | 3/1988 | Palmaz . | |
| 4,740,207 | 4/1988 | Kreamer | 623/1 |
| 4,763,653 | 8/1988 | Rockey | 606/194 |
| 4,773,899 | 9/1988 | Spears | 604/96 |
| 4,799,479 | 1/1989 | Spears | 606/7 |
| 4,842,575 | 6/1989 | Hoffman, Jr. et al. | 600/36 |
| 4,878,492 | 11/1989 | Sinofsky et al. | 128/395 |
| 4,969,912 | 11/1990 | Kelman et al. | 128/DIG. 8 |
| 4,994,033 | 2/1991 | Shockey et al. | 606/194 |
| 5,019,075 | 5/1991 | Spears et al. | 606/7 |
| 5,213,580 | 5/1993 | Slepian et al. . | |
| 5,328,471 | 7/1994 | Slepian . | |

FOREIGN PATENT DOCUMENTS 8912478 12/1989 WIPO .

OTHER PUBLICATIONS

*Science*, vo. 232, Jun. 13, 1986, pp. 1421–1422.

*Primary Examiner*—Gary Jackson
*Assistant Examiner*—Nancy Mulcare
*Attorney, Agent, or Firm*—Arthur Z. Bookstein

[57] ABSTRACT

An uncured or partially cured, collagen-based material is delivered to a selected site in a blood vessel and is crosslinked in the blood vessel by laser energy or other suitable energy to form an endovascular stent. The collagen-based material can be delivered to the blood vessel as a coating on an inflatable balloon mounted on the distal end of a catheter. The collagen-based material can also be delivered to the blood vessel in liquid form. The liquid collagen-based material is forced through a porous balloon to form either an imperforate tubular configuration or a tubular mesh configuration. The collagen-based material is preferably crosslinked by laser radiation carried through an optical fiber to a diffusing tip located within the balloon.

29 Claims, 3 Drawing Sheets

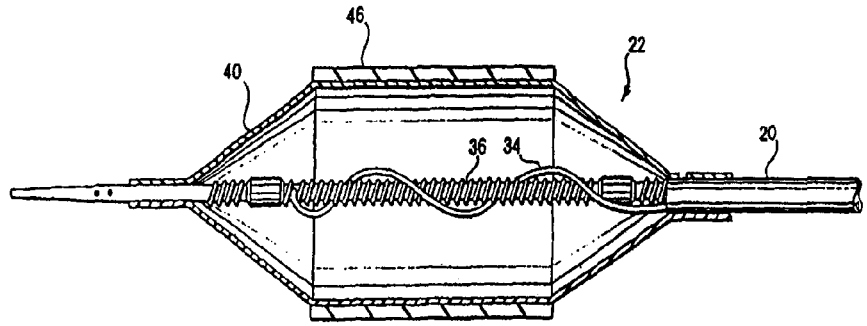

UNITED STATES PATENT AND TRADEMARK OFFICE
CERTIFICATE OF CORRECTION

PATENT NO. : 6,004,261
DATED : December 21, 1999
INVENTOR(S) : Sinofsky et al.

It is certified that error appears in the above-identified patent and that said Letters Patent is hereby corrected as shown below:

Column 10 cont'd.
Line 26, please delete "An endovascular stent" and insert -- A device -- therefor.
Line 29, please delete "An endovascular stent" and insert -- A device -- therefor.

Drawings,
Please delete FIGS. 1-7 and insert the following FIGS. 1-5, therefor.

Fig 1:

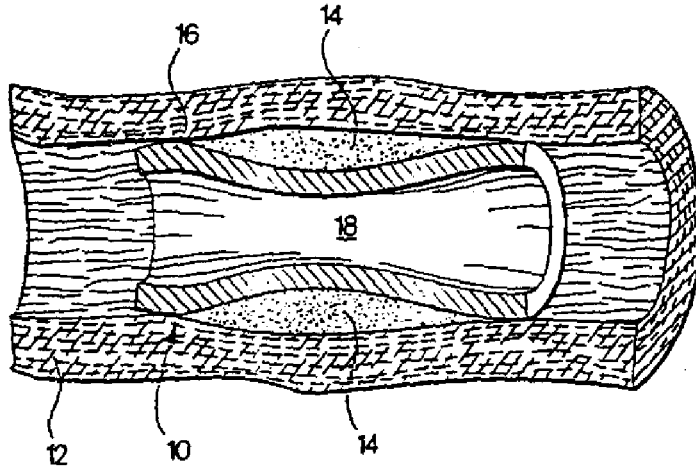

Fig. 1

UNITED STATES PATENT AND TRADEMARK OFFICE
CERTIFICATE OF CORRECTION

PATENT NO. : 6,004,261
DATED : December 21, 1999
INVENTOR(S) : Sinofsky et al.

It is certified that error appears in the above-identified patent and that said Letters Patent is hereby corrected as shown below:

Figs. 2 and 3:

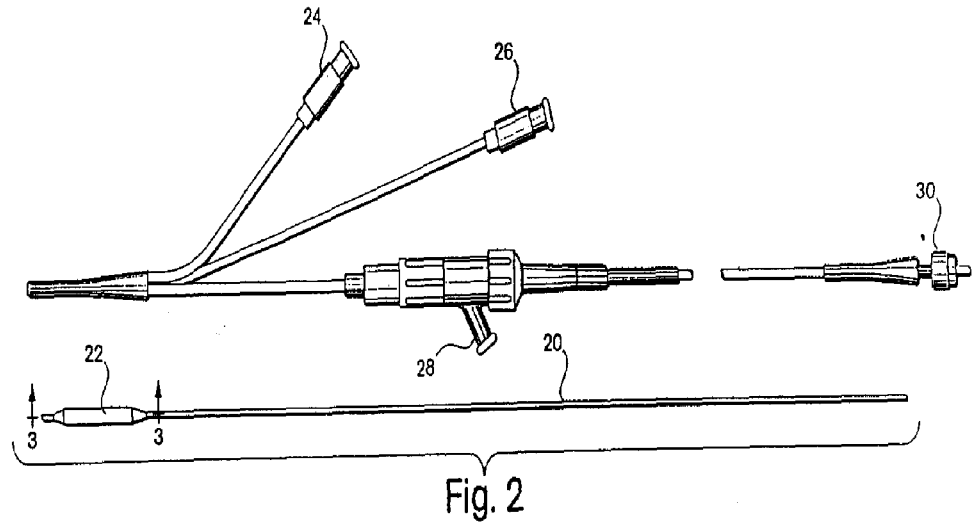

Fig. 2

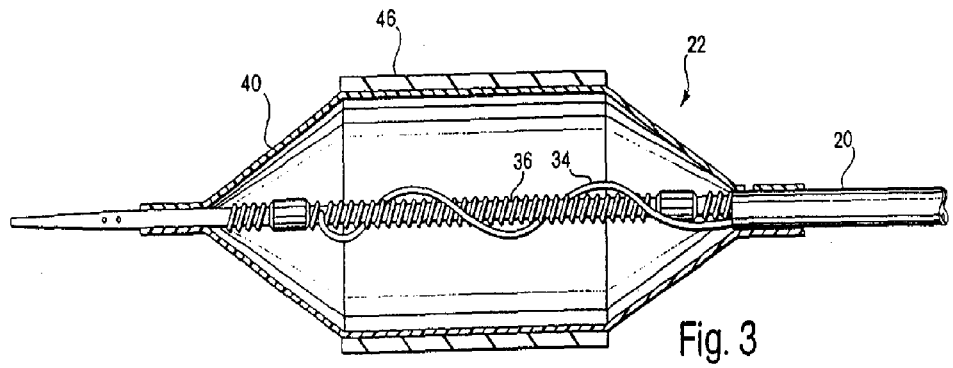

Fig. 3

UNITED STATES PATENT AND TRADEMARK OFFICE
CERTIFICATE OF CORRECTION

PATENT NO.     : 6,004,261
DATED          : December 21, 1999
INVENTOR(S)    : Sinofsky et al.

It is certified that error appears in the above-identified patent and that said Letters Patent is hereby corrected as shown below:

Figs. 4 and 5:

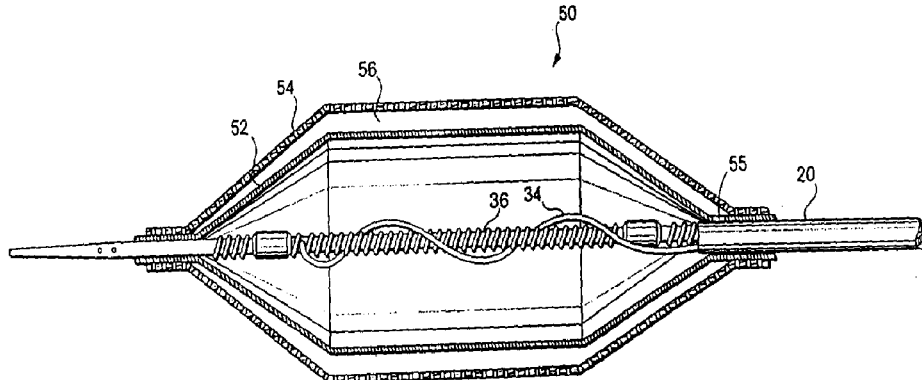

Fig. 4

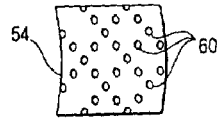

Fig. 5

This certificate supercedes Certificate of Correction issued July 30, 2002.

Signed and Sealed this

Twelfth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,004,261
DATED : December 21, 1999
INVENTOR(S) : Sinofsky et al.

It is certified that error appears in the above-identified patent and that said Letters Patent is hereby corrected as shown below:

Title page,
Delete title page and insert the title page attached.
Item [63], "Related U.S. Application Data" after "abandoned", please insert -- , which is a continuation of Application No. 07/666,424, March 8, 1991, abandoned, which is a continuation of Application No. 07/345,110, April 28, 1989, abandoned --.

Column 1,
Line 5, after "abandoned", please insert -- , which is a continuation of Application No. 07/666,424, March 8, 1991, abandoned, which is a continuation of Application No. 07/345,110, April 28, 1989, abandoned --.

Column 4,
Line 16, please delete "FIGS. 5-7 are fragmentary views" and insert -- FIG. 5 is a fragmentary view --, therefor.

Column 8,
Line 4, please delete "releaseably" and insert -- releasably -- therefor.
Line 18, please delete "than" and insert -- that -- therefor.

Column 9,
Line 29, please delete "11 or 12" and insert -- 19 or 20 -- therefor.

Column 10,
Line 4, please delete "11 or 12" and insert -- 19 or 20 -- therefor.
Beginning at line 25, please delete claim 27, and insert:

-- 27. A crosslinkeable endovascular stent and endovascular delivery device for placement of the stent, in crosslinked form, in a blood vessel comprising, in combination:
a pliable body having a lumen therethrough, the body being formed from a material crosslinkable in response to application of energy, to a state having sufficient rigidity to support the blood vessel from within;
a delivery catheter having an expandable member thereon, the expandable member being disposed within the lumen of the crosslinkable stent;
the crosslinkable stent being radially expandable within the blood vessel by the expandable member on the catheter. --.

United States Patent [19]

Sinofsky et al.

[11] Patent Number: 6,004,261
[45] Date of Patent: Dec. 21, 1999

[54] FORMED-IN-PLACE ENDOVASCULAR STENT AND DELIVERY SYSTEM

[75] Inventors: Edward L. Sinofsky, Peabody, Mass.; Scott J. Solano, Lake Jackson, Tex.; James F. Crittenden, Hollis, N.H.

[73] Assignee: C. R. Bard, Inc., Murray Hill, N.J.

[21] Appl. No.: 08/799,991

[22] Filed: Feb. 13, 1997

Related U.S. Application Data

[63] Continuation of application No. 08/073,277, Jun. 4, 1993, abandoned.

[51] Int. Cl.$^6$ ............................... A61F 1/00; A61F 2/15
[52] U.S. Cl. ................... 600/36; 623/1; 623/12; 604/96; 604/101; 128/395
[58] Field of Search .................. 623/1, 12; 600/36; 604/96, 101; 128/395, 398, 899, 397; 606/7, 8, 13–15, 192–195

[56] References Cited

U.S. PATENT DOCUMENTS

| | | | |
|---|---|---|---|
| 3,173,418 | 3/1965 | Baran . | |
| 3,563,925 | 2/1971 | Kliment et al. | 260/8 |
| 3,625,745 | 12/1971 | Wright | 117/93.31 |
| 3,808,113 | 4/1974 | Okamura et al. . | |
| 3,949,073 | 4/1976 | Daniels et al. | 424/117 |
| 4,060,081 | 11/1977 | Yannas et al. | 128/156 |
| 4,319,363 | 3/1982 | Ketharanathan | 3/1.4 |
| 4,378,017 | 3/1983 | Kosugi et al. | 424/35 |
| 4,390,519 | 6/1983 | Sawyer | 424/28 |
| 4,403,612 | 9/1983 | Fogarty . | |
| 4,417,576 | 11/1983 | Baran | 128/207.15 |
| 4,423,725 | 1/1984 | Baran et al. | 128/207.15 |
| 4,445,892 | 5/1984 | Hussein et al. | 604/101 |
| 4,485,096 | 11/1984 | Bell | 424/95 |
| 4,503,569 | 3/1985 | Dotter | 3/1.4 |
| 4,553,545 | 11/1985 | Maass et al. . | |
| 4,553,974 | 11/1985 | Dewanjee | 8/94.11 |
| 4,577,631 | 3/1986 | Kreamer . | |
| 4,578,067 | 3/1986 | Cran, Jr. | 604/380 |
| 4,589,882 | 5/1986 | Urry | 623/11 |
| 4,597,762 | 7/1986 | Walter et al. | 623/1 |
| 4,605,406 | 8/1986 | Cahalan et al. | 623/1 |
| 4,641,653 | 2/1987 | Rockey | 604/96 |
| 4,642,118 | 2/1987 | Kuroyanagi et al. | 623/15 |
| 4,695,281 | 9/1987 | Miyata et al. | 623/11 |
| 4,704,131 | 11/1987 | Noishiki et al. | 623/66 |
| 4,708,718 | 11/1987 | Daniels | 128/DIG. 8 |
| 4,732,152 | 3/1988 | Wallsten et al. . | |
| 4,733,665 | 3/1988 | Palmaz . | |
| 4,740,207 | 4/1988 | Kreamer | 623/1 |
| 4,763,653 | 8/1988 | Rockey | 606/194 |
| 4,773,899 | 9/1988 | Spears | 604/96 |
| 4,799,479 | 1/1989 | Spears | 606/7 |
| 4,842,575 | 6/1989 | Hoffman, Jr. et al. | 600/36 |
| 4,878,492 | 11/1989 | Sinofsky et al. | 128/395 |
| 4,969,912 | 11/1990 | Kelman et al. | 128/DIG. 8 |
| 4,994,033 | 2/1991 | Shockey et al. | 606/194 |
| 5,019,075 | 5/1991 | Spears et al. | 606/7 |
| 5,213,580 | 5/1993 | Slepian et al. . | |
| 5,328,471 | 7/1994 | Slepian . | |

FOREIGN PATENT DOCUMENTS

8912478  12/1989  WIPO .

OTHER PUBLICATIONS

*Science*, vo. 232, Jun. 13, 1986, pp. 1421–1422.

*Primary Examiner*—Gary Jackson
*Assistant Examiner*—Nancy Mulcare
*Attorney, Agent, or Firm*—Arthur Z. Bookstein

[57] ABSTRACT

An uncured or partially cured, collagen-based material is delivered to a selected site in a blood vessel and is crosslinked in the blood vessel by laser energy or other suitable energy to form an endovascular stent. The collagen-based material can be delivered to the blood vessel as a coating on an inflatable balloon mounted on the distal end of a catheter. The collagen-based material can also be delivered to the blood vessel in liquid form. The liquid collagen-based material is forced through a porous balloon to form either an imperforate tubular configuration or a tubular mesh configuration. The collagen-based material is preferably crosslinked by laser radiation carried through an optical fiber to a diffusing tip located within the balloon.

29 Claims, 3 Drawing Sheets

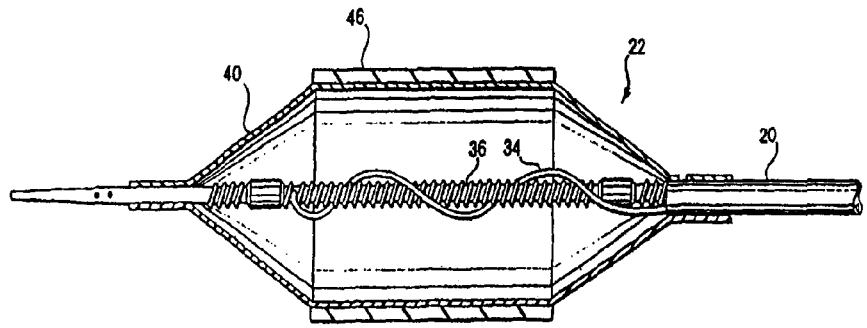

UNITED STATES PATENT AND TRADEMARK OFFICE
CERTIFICATE OF CORRECTION

PATENT NO. : 6,004,261
DATED : December 21, 1999
INVENTOR(S) : Sinofsky et al.

It is certified that error appears in the above-identified patent and that said Letters Patent is hereby corrected as shown below:

Column 10 cont'd.
Line 26, please delete "An endovascular stent" and insert -- A device -- therefor.
Line 29, please delete "An endovascular stent" and insert -- A device -- therefor.

Drawings,
Please delete FIGS. 1-7 and insert the following FIGS. 1-5, therefor.

Fig 1:

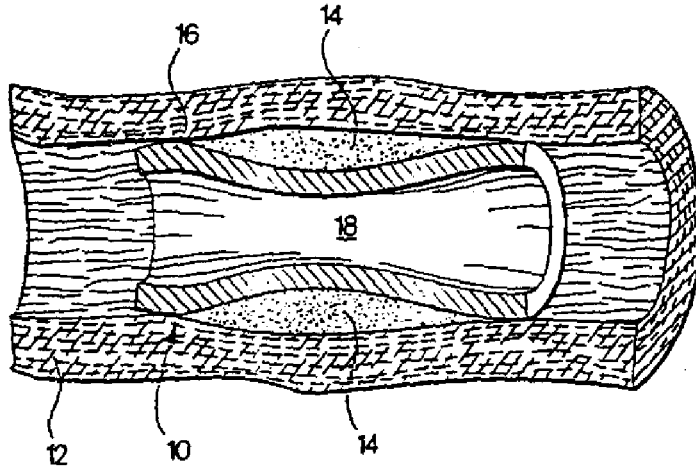

Fig. 1

UNITED STATES PATENT AND TRADEMARK OFFICE
CERTIFICATE OF CORRECTION

PATENT NO.     : 6,004,261                                        Page 4 of 5
DATED          : December 21, 1999
INVENTOR(S)    : Sinofsky et al.

It is certified that error appears in the above-identified patent and that said Letters Patent is hereby corrected as shown below:

Figs. 2 and 3:

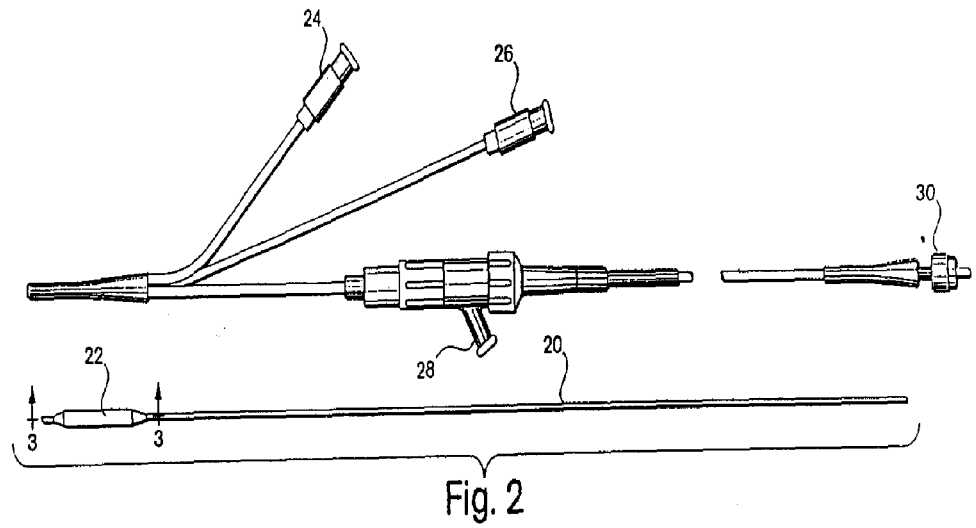

Fig. 2

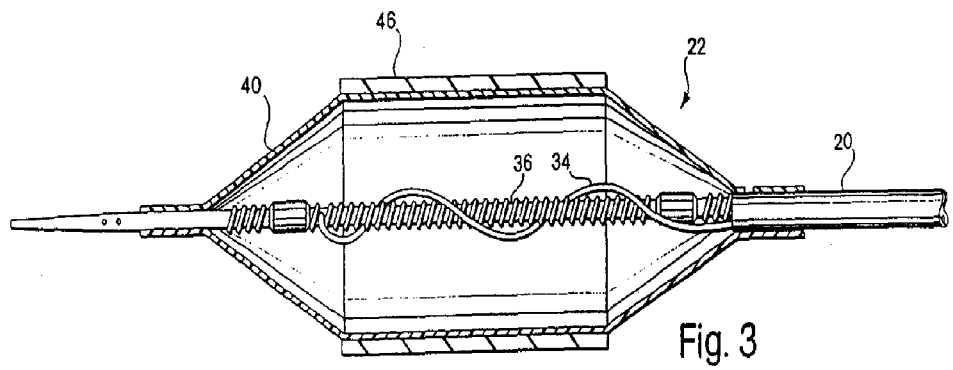

Fig. 3

UNITED STATES PATENT AND TRADEMARK OFFICE
CERTIFICATE OF CORRECTION

PATENT NO.   : 6,004,261    Page 5 of 5
DATED        : December 21, 1999
INVENTOR(S)  : Sinofsky et al.

It is certified that error appears in the above-identified patent and that said Letters Patent is hereby corrected as shown below:

Figs. 4 and 5:

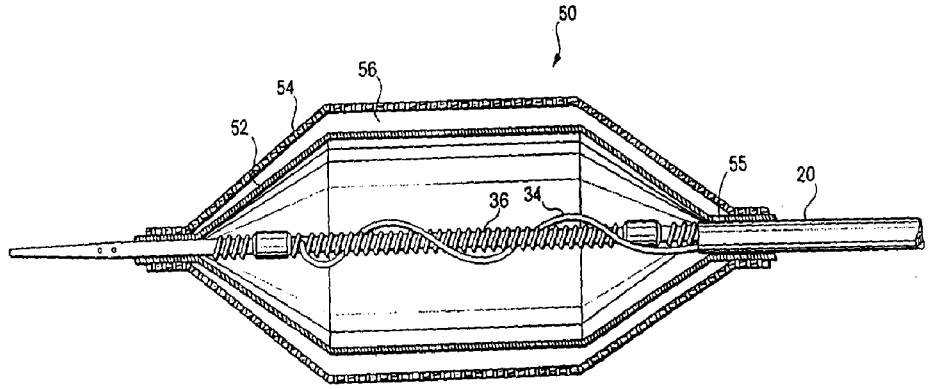

Fig. 4

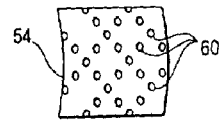

Fig. 5

This certificate supersedes Certificate of Correction issued July 30, 2002.

Signed and Sealed this

Nineteenth Day of November, 2002

*Attest:*

*Attesting Officer*

JAMES E. ROGAN
*Director of the United States Patent and Trademark Office*